US008366932B1

(12) United States Patent
Sung et al.

(10) Patent No.: US 8,366,932 B1
(45) Date of Patent: Feb. 5, 2013

(54) MICRO-AERATION OF SULFIDE REMOVAL FROM BIOGAS

(75) Inventors: Shihwu Sung, Ames, IA (US); Samir Kumar Khanal, Honolulu, HI (US); Thanapong Duangmanee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 489 days.

(21) Appl. No.: 12/564,581

(22) Filed: Sep. 22, 2009

Related U.S. Application Data

(60) Provisional application No. 61/103,775, filed on Oct. 8, 2008.

(51) Int. Cl.
*C02F 3/28* (2006.01)
*B01D 53/52* (2006.01)
(52) U.S. Cl. .................. 210/603; 210/758; 423/224
(58) Field of Classification Search .................. 210/603, 210/631, 758; 423/224
See application file for complete search history.

(56) References Cited

U.S. PATENT DOCUMENTS

| 3,388,057 | A | * | 6/1968 | Callahan | 210/603 |
| 3,876,535 | A | * | 4/1975 | Young | 210/604 |
| 4,511,544 | A | * | 4/1985 | Connell et al. | 423/576.2 |
| 4,534,955 | A | * | 8/1985 | Rosenbaum | 423/576.2 |
| 4,919,814 | A | * | 4/1990 | Carnahan et al. | 210/603 |
| 5,298,163 | A | * | 3/1994 | Ehlinger | 210/603 |
| 5,403,567 | A | * | 4/1995 | Smith et al. | 423/210 |
| 5,730,784 | A | * | 3/1998 | Smith et al. | 95/181 |
| 5,861,096 | A | * | 1/1999 | Mason et al. | 210/631 |
| 5,958,238 | A | * | 9/1999 | Langerwerf | 210/603 |
| 6,036,862 | A | * | 3/2000 | Stover | 210/603 |
| 7,279,148 | B1 | * | 10/2007 | Nagl et al. | 423/576.2 |
| 7,708,885 | B2 | * | 5/2010 | Lanting et al. | 210/603 |
| 2003/0141243 | A1 | * | 7/2003 | Groenestijn et al. | 210/603 |

FOREIGN PATENT DOCUMENTS

| EP | 0418121 A1 | * | 3/1991 |
| JP | 5-68849 A | * | 3/1993 |

OTHER PUBLICATIONS

Khanal, et al., "ORP-based Oxygenation for Sulfide Control in Anaerobic Treatment of High-sulfate Wastewater", Water Research, 37(9):253-262 (2003).
Khanal, et al., "Effect of High Influent Sulfate on Anaerobic Wastewater Treatment", Water Environmental Research, 77(7):3037-3046 (2005).
Khanal, et al., "Anaerobic Treatment of High Sulfate Wastewater with Oxygenation to Control Sulfide", Journal of Environmental Engineering, 129(12)1104-1111 (2003).
Khanal, et al., "Use of ORP (oxidation-reduction potential) to control oxygen dosing for online sulfide oxidation in anaerobic treatment of high sulfate wastewater", Water Science Technology, 47(12):193-199 (2003).
Huang, et al., "Treatment of high sulfate and high strength wastewater in a single stage anaerobic reactor", Water Science Technology: Water Supply, 4(1):35-45 (2004).
Khanal, et al., "Online Oxygen Control for Sulfide Oxidation in Anaerobic Treatment of High-Sulfate Wastewater", Water Environmental Research, 78(4):397-408 (2006).

* cited by examiner

*Primary Examiner* — Fred Prince
(74) *Attorney, Agent, or Firm* — McKee, Voorhees & Sease, P.L.C.

(57) ABSTRACT

A novel method for treating sulfide-containing wastewater is described which involves treating sulfide-laden biogas produced in a bioreactor in a sulfide oxidizing unit (SOU). Oxidation in the SOU is monitored by an oxidation reduction potential (ORP) probe which minimizes the input of air/oxygen to produce elemental sulfur without significant production of sulfate.

15 Claims, 7 Drawing Sheets

SCHEMATIC DIAGRAM OF THE PRIOR ART

MICRO-AERATION OF SULFIDE REMOVAL FROM BIOGAS

CROSS-REFERENCE TO RELATED APPLICATIONS

This application claims priority under 35 U.S.C. §119 of a provisional application Ser. No. 61/103,775 filed Oct. 8, 2008, which application is hereby incorporated by reference in its entirety.

GRANT REFERENCE CLAUSE

This invention was funded at least in part by the USDA Contract No. 2002-34188-12035. The government may have certain rights in this invention.

FIELD OF THE INVENTION

This invention relates to the removal of sulfide from biogas, wastewater and other liquid streams.

BACKGROUND OF THE INVENTION

In recent years especially, governmental regulators have provided stringent parameters for controlling environmental pollution. The typical parameters for monitoring such pollution and the efficiency of any treatment system are COD (chemical oxygen demand) and BOD (biochemical oxygen demand). Anaerobic processing has been widely adopted to stabilize wastes/wastewater due to its several inherent merits, such as generation of renewable energy—methane, less sludge production, lower energy consumption than its aerobic counterpart, etc. However, in many cases, industrial wastewater contains sulfur compounds (e.g. sulfate, thiosulfate, sulfite, etc.). If present in the wastewater, these sulfur compounds are converted to highly corrosive and odorous hydrogen sulfide ($H_2S$) under anaerobic conditions. The high sulfide level in the biogas stream is not only detrimental to many novel metal catalysts employed in thermo-catalytic processes, but also reduces the quality of methane as a renewable energy. Moreover, aqueous sulfide in the bioreactor inhibits methanogenesis, the main pathway for methane production in anaerobic processes, which in turn significantly reduces the yield of methane.

When wastes containing sulfur compounds are fed to the digester, sulfate reducing bacteria (SRB), such as Desulfovibrio, Desulfotomaculum, Desulfobacter, Desulfosarcina, and Desulfococcus, will reduce sulfur containing compounds to sulfides, resulting in biogas contaminated with hydrogen sulfide by the following equations:

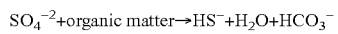

$$SO_4^{-2} + \text{organic matter} \rightarrow HS^- + H_2O + HCO_3^-$$

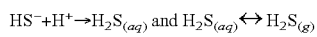

$$HS^- + H^+ \rightarrow H_2S_{(aq)} \text{ and } H_2S_{(aq)} \leftrightarrow H_2S_{(g)}$$

The hydrogen sulfide in biogas limits the usage of biogas in many downstream processes. For instance, heat production using a boiler requires hydrogen sulfide to be less than 1000 ppmV whereas hydrogen sulfide limitation in electricity production by internal combustion engine is only 100 ppmV. To inject methane generated from digester into a pipeline, hydrogen sulfide concentration needs to be less than 4 ppmV. Some other novel catalytic processes to convert methane to other useful ingredients in some products, such as biodiesel, require the presence of no hydrogen sulfide. In addition, burning of biogas containing hydrogen sulfide produces sulfur oxides, which are a main precursor of acid rain. Besides hydrogen sulfide in off-gas, if sulfides in liquid are released to receiving steams, they are toxic to aquatic life and deplete oxygen concentration.

Methods to remove hydrogen sulfide from biogas stream consist mainly of chemical, physical and/or biological processes. Chemical processes involve adding chemicals into liquid containing sulfides to either oxidize sulfides or shift volatile sulfide, hydrogen sulfide, to nonvolatile forms (sulfide and bisulfide). Such chemicals are alkaline solutions, chlorine, ozone, potassium permanganate, hydrogen peroxide, and nitrite. However, the dosage of the oxidizing agents can be problematic since not only do the agents oxidize sulfide, but also other organic and inorganic compounds present in wastewater. Thus, the addition of chlorine or nitrite to wastewater produces unwanted byproducts such as carcinogenic trihalomethane (THM), NOx, and ammonia.

Physical processes of removing hydrogen sulfide involve the use of metal oxides (e.g. iron and zinc oxides), alkaline solutions, zinc acetate, ferrous chloride molecular sieve, activated carbon, etc. to react with sulfide. However, these processes are high-cost, and provide a chemical disposal problem. The sulfide removal activity is deteriorated over a short period of time unless the absorbents are replaced, resulting in recurring expenses. In addition, the precipitates formed may greatly reduce the active volume of the digester.

Biological processes involve utilizing aerobic chemoautotroph or anaerobic photoautotroph to oxidize sulfides in both gas and liquid phases to elemental sulfur. The sulfide removal rates of the biological processes are comparable to that of the chemical or physical processes. Moreover, biologically-produced sulfur is known as a better substrate for bioleaching of heavy metal contamination from wastes, such as swine manure.

In biological sulfide removal from gas or liquid streams, elemental sulfur is preferred as a final product. Since elemental sulfur is insoluble, it can be removed from the streams relatively easily, which results in reduction of the overall sulfur species. Sulfide oxidation to elemental sulfur requires four times less oxygen than the oxidation to sulfate; therefore, the energy consumption through aeration can greatly be reduced.

To gear the biological sulfide oxidation to sulfur formation, the supply of oxygen needs to be optimized. If the molar ratio of oxygen/sulfide consumption is at two or more, sulfate will be the major product. However, if the oxygen/sulfide ratio is approximately at 0.5, then the majority of the products will be elemental sulfur. By monitoring and controlling the molar ratio of oxygen/sulfide consumption in a biological sulfide oxidizing reactor, it is possible to prevent sulfur from being oxidized to sulfate. This can be achieved by removal of formed sulfur as soon as possible via better reactor design.

Most research on removal of sulfide has focused on the treatment of dilute wastewater. Little attention has been paid to high-solids wastewater, such as animal waste (total solids 2%-6%). The use of packed media in anaerobic digester or in sulfide oxidizing reactors prevents them from being useful in treating high-solids waste due to the potential of clogging.

There is therefore a need in the art for a novel approach for removing sulfide from biogas with maximum sulfur recovery but minimal sulfate production. There is a further need for a method of removing sulfide from high-solids wastewater. Further objectives include:

(i) to develop a process and system which micro-aeration to achieve selective sulfide oxidation to elemental sulfur;
(ii) to develop a sulfide-free biogas (<10 ppmV) with minimal oxygen (<2%) in biogas and sulfide free effluent;

(iii) to develop a process in which one can treat high solids wastewater (2%-6% TS) (total solids), such as those from agriculture residues;

(iv) to develop process and system that does not rely on microorganism addition; and (v) to provide an efficient system that avoids chemical addition for oxidizers or pH adjustment.

The method of accomplishing these and other objectives will be apparent from the following detailed description.

SUMMARY OF THE INVENTION

The present invention relates to the development of technology to remove sulfide from biogas wastewater and other water streams without disturbing methanogenesis. The process involves the use of a micro-aeration technique controlled by ORP (Oxidation-Reduction Potential) whereby sulfide is oxidized to elemental sulfur to the preferred exclusion of sulfate. The process has been shown to successfully remove sulfides in the gas stream, to a level of <10 ppmV, and as low as <1 ppmV with minimal oxygen (<2%).

The invention generally includes a set of diffusers, a gas recirculation and/or air/oxygen injection control and monitoring system that can be attached to any sulfide producing bioreactor/unit. A unique aspect is the use of a separated sulfide oxidizing unit (SOU) in which air/oxygen is injected into the sulfide-rich biogas produced from the digester to oxidize the sulfide to elemental sulfur and produce sulfide-free biogas while preventing further oxidation of the sulfur to sulfate through the use of an ORP (oxidative-reduction potential) electrode. In some cases, where it is preferable to remove sulfide in the digester, the sulfide-free biogas is recirculated to the digester whereby it is injected to further absorb sulfide existing in the digester medium.

DETAILED DESCRIPTION OF THE DRAWINGS

DETAILED DESCRIPTION OF THE INVENTION

As already noted, the present invention is directed to a unique method and apparatus or system for removing sulfide from bioreactor/sulfide producing systems. In prior designs, bioreactor/sulfide producing systems were designed without a micro-aeration control system, thus allowing the formation of toxic sulfide. The present invention is designed to simultaneously remove sulfides from both gaseous and aqueous phases. While prior art bioreactors having micro-aeration are designed for handling dilute waste, the current invention is designed to handle both dilute and high solids wastewater (2-6% total solids), such as those from agricultural residues. The design of the invention is applicable not only to clean-up of sulfide from waste and wastewater, but also to any industrial process requiring sulfide-free gas/liquid for downstream use.

Figure 1:
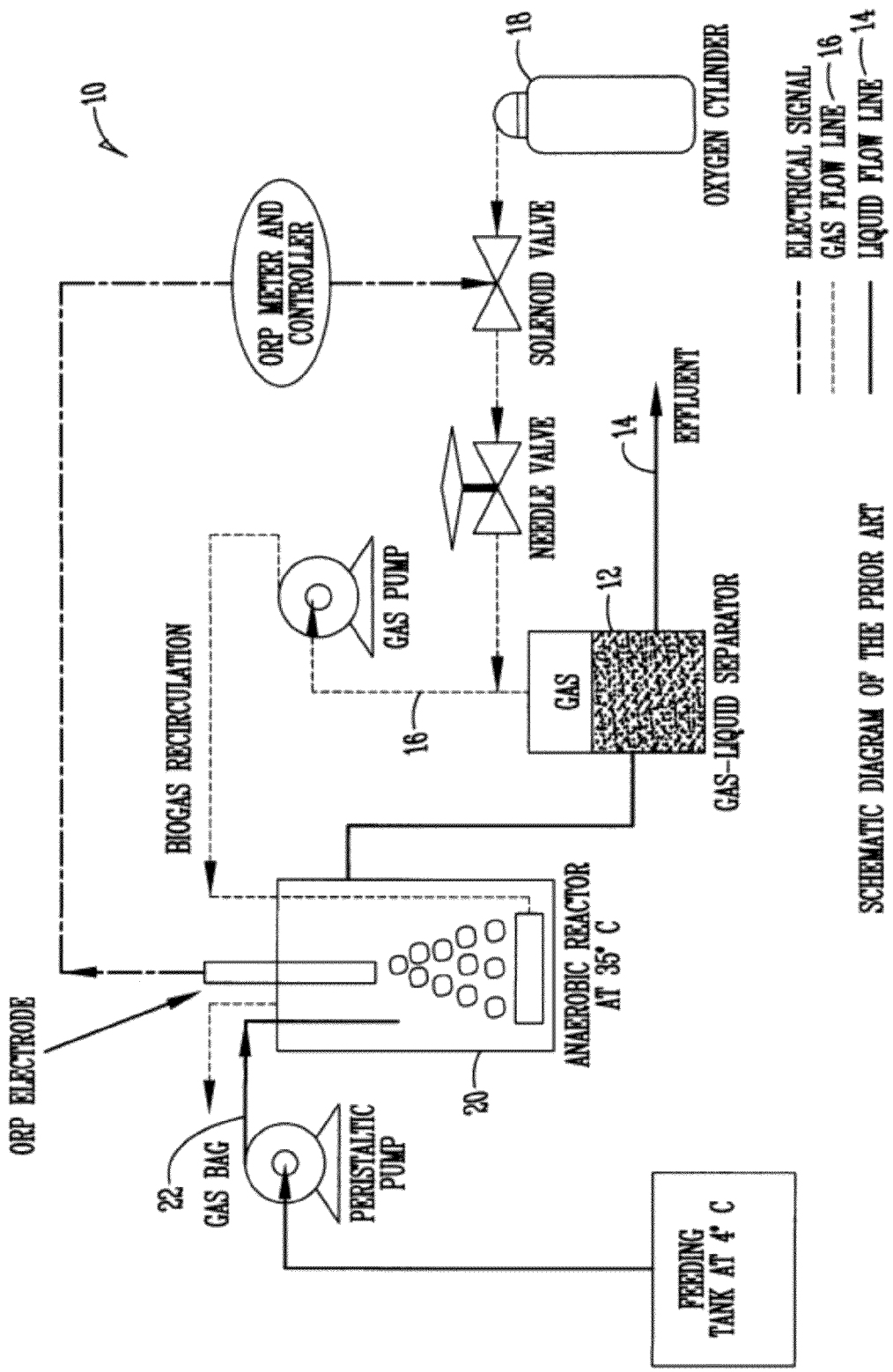
FIG. 1 illustrates a prior art reactor set-up designed to remove sulfide.

FIG. 1 illustrates one type of prior art reactor 10 meant to remove sulfide so that the toxicity imposed by the sulfide in the reactor is alleviated. See Khanal et al. (2003) ORP-based Oxygenation for Sulfide Control in Anaerobic Treatment of High-Sulfate Wastewater. *Wat. Res.*, 37 (9), 2053-2062); Khanal et al. (2005) Effect of High Influent Sulfate on Anaerobic Wastewater Treatment. *Water Environ. Res.*, 77(7), 3037-3046. As shown, such devices 10 include gas-liquid separators 12 designed merely to divide liquid 14 from the gas streams 16, but not to actually remove hydrogen sulfide from the gas stream. The present invention offers several advantages over such systems. First, as noted, the main focus of such devices is treatment of high-sulfate (1000-5000 mg/L) diluted wastewater to eliminate sulfide toxicity on methanogens, while the focus of the current invention is treatment of high-solids content wastewater to remove gaseous hydrogen sulfide from biogas. Further, the prior art device injects air/oxygen 18 directly into the reactor 20 with the intention of oxidizing the sulfide in the reactor 18 fed with the influent 22 to sulfur. In many instances, however, the sulfur produced is subsequently reduced back to sulfide due to the methane conditions of the reactor 18. In contrast, the present invention oxidizes the sulfide to sulfur within the separate SOU, whereby the sulfur is collected and discharged from the system. Furthermore, the present invention offers the advantage of ORP and pH probes in the SOU to constantly monitor the ORP and pH in the SOU and control the frequency and duration of air/oxygen injection based upon these factors.

Figure 2:
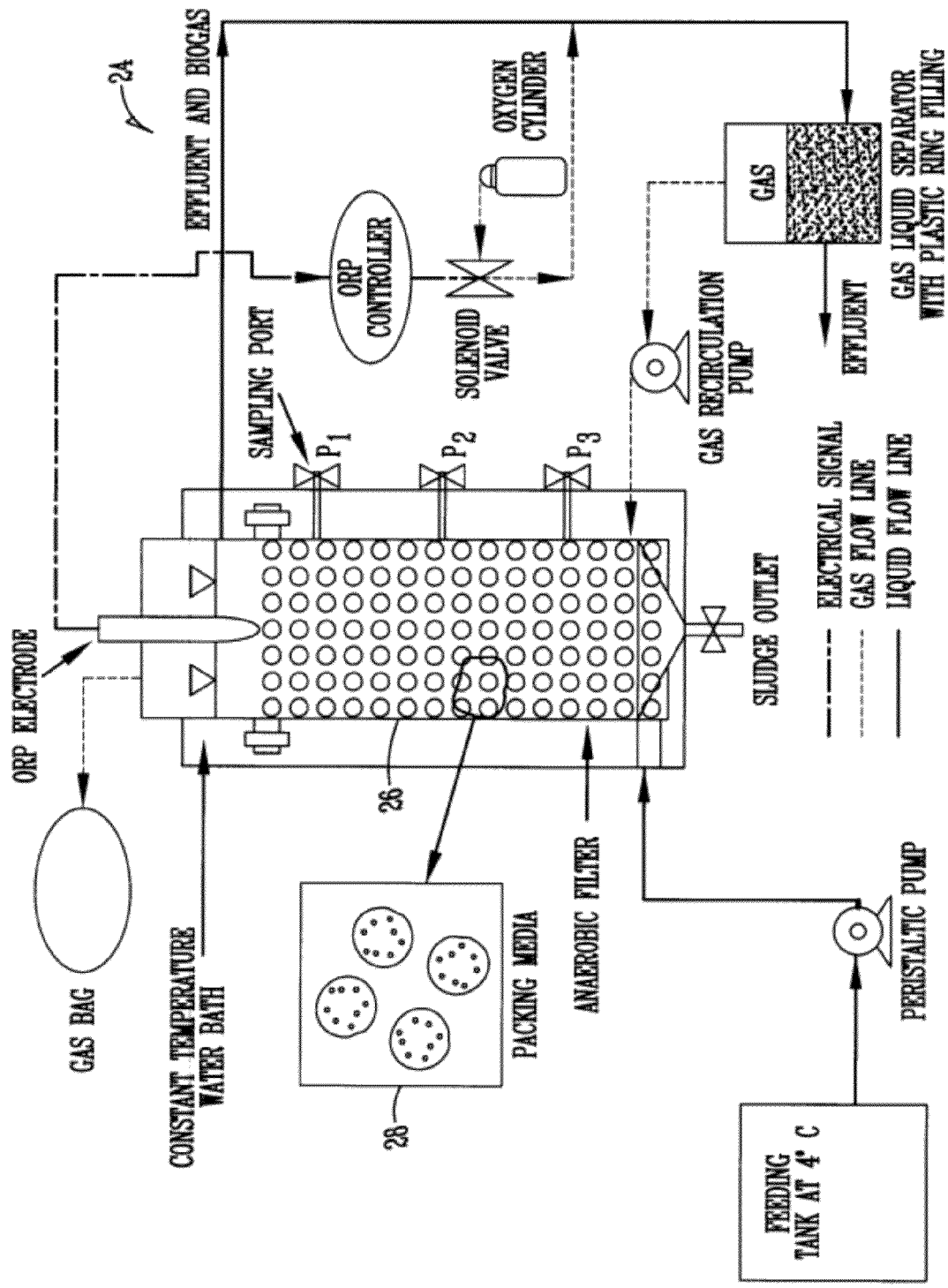
FIG. 2 illustrates a second prior art reactor set-up designed to remove sulfide.

FIG. 2 illustrates an alternative prior art setup 24 having an SOU 26 filled with plastic media. See Khanal et al. (2003) Anaerobic Treatment of High Sulfate Wastewater with Oxygenation to Control Sulfide Toxicity. *J. Env. Eng.*, 129(12), 1104-1111. In comparison, the SOU of the present invention has a height of greater than two feet to maximize absorption of hydrogen sulfide and oxygen, thus eliminating the need for packing material 28. In addition, the device of the prior art 24 shown is limited to low-solid (<0.1% total solids) wastewater only, while there is no limitation on the solids content of the wastewater that can be treated using the apparatuses of the present invention.

As noted, while prior art devices utilize ORP probes only in the bioreactor 20, 26, the present invention (FIG. 3) has a separate ORP probe 30 in the SOU to limit overaeration. This in turn allows for continuous removal of sulfide from both the gaseous and liquid phases of the waste stream without disruption of methanogenesis. As ORP varies linearly with the logarithm of oxygen concentration, even a small dosing is instantaneously sensed by the ORP electrode. By doing so, sulfides in the biogas and liquid are selectively converted to terminal end-product, elemental sulfur, which can be reused in the bioleaching of heavy metals, as an electron donor in denitrification, as a fertilizer, fungicide, etc.

In accordance with the invention, the key element to oxidation of sulfides is controlling the ratio of $O_2/S^{2-}$. The relevant reactions are as follows:

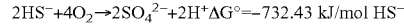

$$2HS^- + 4O_2 \rightarrow 2SO_4^{2-} + 2H^+ \Delta G° = -732.43 \text{ kJ/mol } HS^-$$

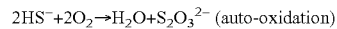

$$2HS^- + 2O_2 \rightarrow H_2O + S_2O_3^{2-} \text{ (auto-oxidation)}$$

$$2HS^- + O_2 \rightarrow 2S^0 + 2OH^- \Delta G° = -129.50 \text{ kJ/mol } HS^-$$

As the oxidation of sulfide to sulfur is difficult to control, the ORP probes of the invention reflex the sulfide and oxygen concentrations in the process and their effects on ORP, and make sure that air is not injected more than necessary. By doing so, sulfides in biogas and liquid are selectively converted to terminal end-product, elemental sulfur, which can be reused in bioleaching of heavy metals, as an electron donor in denitrification, as fertilizer, fungicide, etc., without overoxidation of the sulfur to sulfate. If there is sulfide in the medium, the ORP is reduced. Adding air to the medium would remove the sulfide and increase the ORP. By setting the ORP to a certain range, the amount of air injected can be precisely controlled according to the sulfide loaded to the SOU.

Numerous industrial processes have a requirement of hydrogen sulfide reduction, as follows:

Microturbines: up to 70,000 ppmV
  Boilers and Stirling engine: <1000 ppmV
  Internal combustion engines: <100 ppmV
  Kitchen stoves and fuel cells: <10 ppmV
  Pipeline-grade high-BTU gas: <4 ppmV The methods of the present invention (FIG. 3) are useful in meeting these standards as they result in removal of $H_{2S}$ from biogas to a level of <10 ppmV, and to as low as <1 ppmV, with minimal oxygen (<2%) and without the addition of microorganisms. The design of the invention is applicable not only to clean up sulfide from waste/wastewater, but also to any industrial process that needs sulfide-free gas/liquid stream for downstream use.

Figure 3:
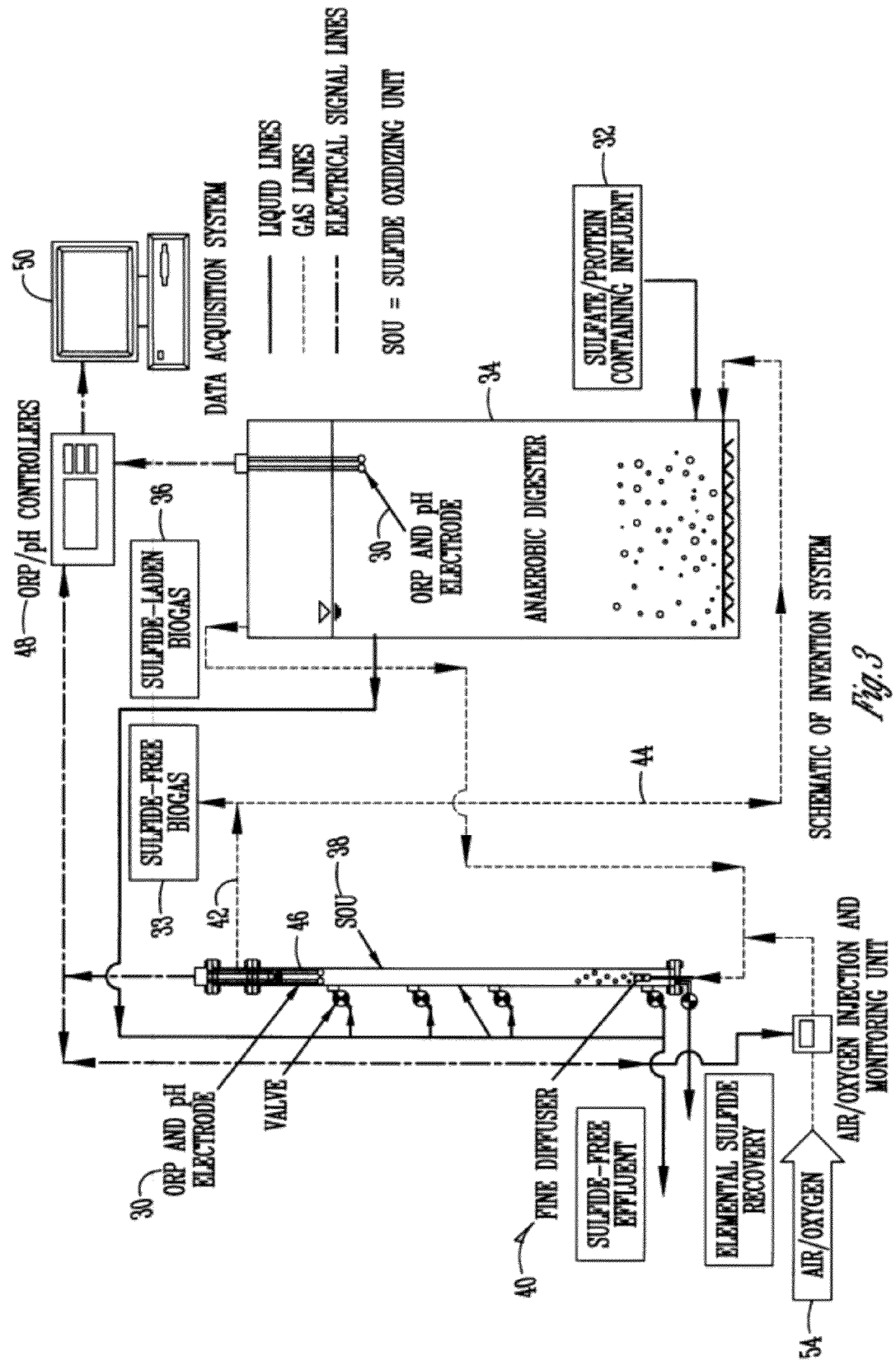
FIG. 3 illustrates a preferred embodiment of the sulfide removal system of the present invention.

The invention first involves treatment of wastes/wastewater FIG. 3, 32 (hereafter cumulatively referred to as wastewater) that is suspected of containing sulfur compounds in a bioreactor/digester 34. The invention may be used to treat any wastewater containing organic, biodegradable solids, either dilute or concentrated. Typical sources of such wastewater include chemical, pharmaceutical, pulp and paper, furfural production, rice and corn milling, molasses fermentation, seafood processing, potato-starch factory, tannery, edible oil refinery, wine distillery, fluid milk and cheese production, petrochemical, brewery and meat packing industries, effluents from acidogenic anaerobic fermentation, as well as effluent from any other industrial processes that use sulfuric acids for pH adjustment and/or chemical reactions. The process of the invention is effective in treating low, medium, and high strength wastewater having a COD up to, and possibly greater than 10,000 mg/L. It is not necessary to combine the wastewater entering the vessel with additional liquid to decrease the amount of total solids. However, the wastewater may be diluted prior to treatment if desired. The feed rate of the wastewater may vary, and depends primarily upon the flow rate from the wastewater source.

In wastewater treatment processes, bioreactors are employed to increase the rate of biodegradation of pollution in liquid streams and can be a more rapid and efficient means of degrading pollution than any of the other treatment processes. The term "bioreactor" as used herein includes any structure having a cavity that could hold a liquid pollution stream. This would include natural structures such as ponds, lakes, swamps, rivers, streams, harbors, and oceans, as well as man-made structures such as tanks, pipes and other storage vessels. It would also include onetime flow through digesters, such as onetime flow through activated sludge digesters, aeration basins, anaerobic or facultative lagoons, and ponds. The processing temperature of the wastewater 32 may generally range from 10° C.-70° C. In one embodiment, the processing temperature is between about 30° C.-40° C. Ambient temperatures are preferred for purposes of cost and convenience.

Depending on the type of feed stream, the bioreactor can be operated at HRT (Hydraulic Retention Time) ranging from 3 hrs to 100 days. The longer HRTs are preferred for medium to high strength wastewater. It may also be preferred to initially run the system at a longer HRT, then shorten the HRT once the system reaches a steady state that varies according to the amount of waste in the wastewater, flow rate, etc.

The system is capable of operating over a wide range of organic loadings, with a typical range of 3.2 to 32 kg-COD/$m^3$/day. The invention works over all ranges of organic loading without upper limit in loading rate. The minimum reactor size is determined by multiplying the HRT by the flow rate.

The wastewater in the digester/reactor produces hydrogen sulfide-containing biogas 36 through anaerobic digestion. In accordance with the invention, this sulfide-laden biogas is transferred from the digester to a Sulfide Oxidizing Unit (SOU) 38 containing liquid. The liquid in the SOU can be any type of water, including treated or untreated wastewater (effluent), water from waste storage lagoon, river water, tap water, distilled water, etc. The water is preferably one that is economical to use, such as effluent. It is also preferred that (1) the water is one that does not contain grease or other contaminants that cause foaming in the SOU, i.e. a liquid with low surface tension; and (2) the water includes low biodegradable materials to consume dissolved oxygen during the sulfide oxidation.

The SOU 38 of the invention can be of any size or shape, with a height that is preferably at least two feet. This height enhances mass transfer, and the ability of the sulfide and oxygen bubbled into the bottom of the SOU to dissolve in the liquid as they rise to the top of the SOU. This design further eliminates the need for packing media and allows the SOU to handle high solids wastes. In a preferred embodiment, the sulfide-laden biogas is bubbled 40 into the SOU at a rate of 0.05 to 5 L-biogas/$L_{sou}$-min. For biological and chemical oxidation, the technology utilizes natural existing sulfur oxidizing microbes and nutrient in the medium, making it unnecessary to inoculate or add microorganisms or nutrient into the SOU 38. The configuration of the SOU 38 depends on the quantity of the biogas, sulfide concentration, oxygen dosing rate, and desired sulfide removal efficiency.

While pure oxygen may be used in the systems of the invention, for reasons of economy, air is preferred. In preferred embodiments of the invention, the air/oxygen is injected into the SOU at a rate of from about 0.1 to 50% of the amount of biogas that is normally produced during the period with or without air/oxygen injection. In general, the injection rate of air/oxygen is from about 0.00005 to 2.5 L-biogas/$L_{sou}$-min (i.e. between 0.1% of 0.05 L/$L_{sou}$-min. and 50% of 5 L/$L_{sou}$-min. The pH is controlled by means of replacing medium in SOU with water. The replacing rate is controlled by HRT. While the type of medium used will primarily dictate the operating pH, as a general rule the pH is preferably more than 7.0, and typically in a range of 4.0-14.0. Since ORP changes when the pH changes, it is preferred to fix the pH during operation so the ORP value can be used to determine the amount of air to inject. The SOU can be operated at HRT of 0.1 to 10 h when using bioreactor effluent or at HRT of 0 (no exchange of liquids) when using other types of liquids.

After air injection, the biogas is passed through a diffuser 40 to dissolve hydrogen sulfide and oxygen into a medium where the two react to form elemental sulfur, sulfate ($SO_4^{2-}$), thiosulfate ($S_2O_3^{2-}$) and other oxidized forms of sulfur. The diffuser is preferably set above the level of settled sulfur at the bottom of the SOU to prevent its agitation and/or disruption, thereby interfering with its removal from the system. After the hydrogen sulfide in the biogas is removed and elemental sulfur formed, excess biogas is discharged 42. In an integrated system of the invention, the sulfide-free biogas is sent back to the digester to mix its content and carry (absorb) newly formed sulfide to be treated in the SOU. The present invention further encompasses the use of the SOU as a standalone unit, i.e. no biogas flowing back 44 to the digester. Such standalone systems are preferred for digesters without sulfide toxicity issues.

The control system consists of a set of ORP 30 and pH probes 46 attached to the SOU. The probes are connected to controllers 48 that control the frequency and duration of air/oxygen injection through valves which are parts of the air/oxygen injection and monitoring unit. The oxygen injection and monitoring unit also comprises a flow meter connected to a computer 50 to determine the amount of air/oxygen injected. The amount of air/oxygen, ORP, and pH values are monitored every second using data acquisition systems. As noted, the ORP is used to control aeration at the SOU to ensure that air is not injected more than necessary, whereby sulfide in the medium reduces ORP, and adding air to the medium removes sulfide and increases ORP. An optional set of ORP and pH probes may be placed in the reactor to further monitor ORP, also such probes are not required.

Sulfide-free liquid effluent is drained from the SOU, and the elemental sulfur in solid form is also easily separated from the liquid via conventional means.

In summary, the technology of the present invention provides an innovative, low-maintenance, low-cost biological sulfide removal process to remove sulfides simultaneously from both gas and liquid phase. The micro-aeration technique provides just enough oxygen to partially oxidize sulfides to elemental sulfur without inhibiting methanogenesis. The system is able to achieve absorption and oxidation of wastewater in a single tank without the addition of oxidizing chemical. Further, in contrast to other biological process which require the addition of nutrient solution to support the growth of bacteria, the present invention does not require inoculation of any microorganism or addition of nutrient solution.

The following examples are offered to illustrate but not limit the invention. Thus, they are presented with the understanding that various formulation modifications as well as reactor modifications may be made and still be within the spirit of the invention.

EXAMPLE 1

Preferred Sulfide Removal Apparatus

A preferred apparatus of the invention is illustrated in FIG. 3. The set-up mainly consists of two gas recirculation loops (FIG. 3). In the first loop, sulfide-laden biogas 32 bubbles at the rate of 0.05 to 5 L-biogas/$L_{column}$-min through a long slender column (SOU—Sulfide Oxidizing Unit) containing liquids. In the second loop, sulfide-free biogas 33 from SOU bubbles through the sulfide producing bioreactor at the rate of 0.0015 to 0.15 L-biogas/$L_{bioreactor}$-min. The two loops are connected to each other as shown in FIG. 3.

The SOU consists of a diffuser 40 at the bottom with liquid and/or gas inlets and/or outlets along the column wall. A small chamber is located at the bottom of the SOU below the diffuser to collect elemental sulfur 52, as well as other particulate matters. The column is also equipped with air/oxygen injection 54 and monitoring unit to inject air/oxygen at the rate of 0.1 to 50% of the amount of biogas that is normally produced during the period with or without air/oxygen injection.

The control system consists of two sets of ORP and pH probes. The first set is installed in the SOU whereas the second set is installed in the bioreactor. The probes are connected to the controllers that control the frequency and duration of air/oxygen injection through solenoid valves which are parts of air/oxygen injection and monitoring unit. The air/oxygen injection and monitoring unit also comprises of a flow meter connected to the computer to determine the amount of air/oxygen injected. The amount of air/oxygen, ORP, and pH values are monitored every second using data acquisition system.

Depending on the type of feed stream, bioreactor can be operated at HRT (Hydraulic Retention Time) ranging from 3 hrs to 100 d. The SOU can be operated at HRT of 0.1 to 10 hr when using bioreactor effluent or at HRT of 0 (no exchange of liquids) when using other types of liquids.

Figure 4:
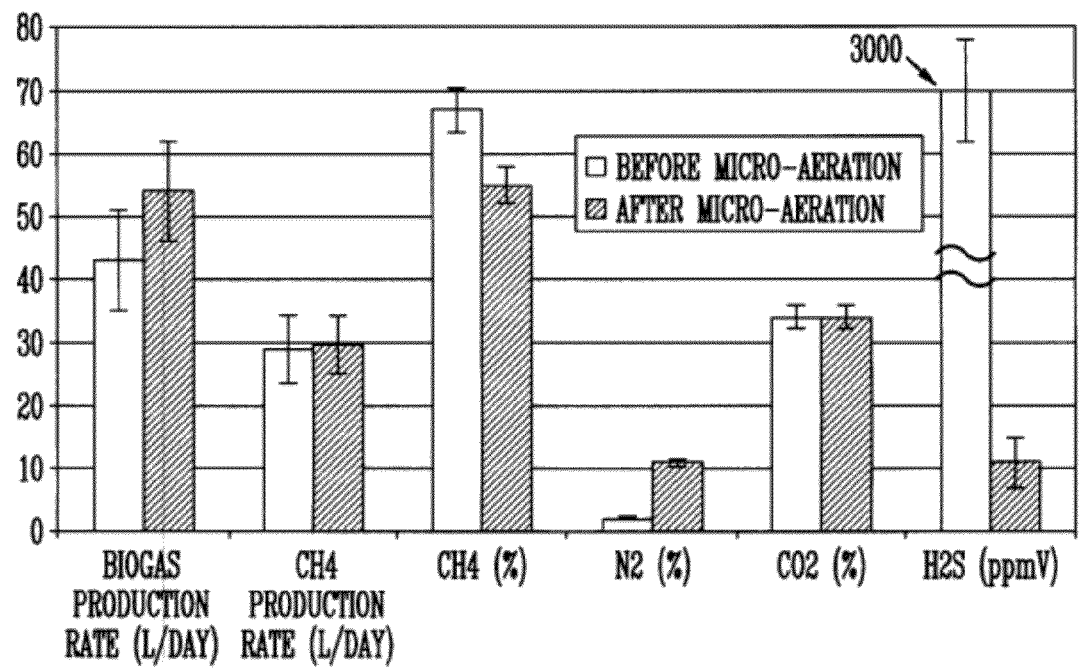
FIG. 4 illustrates the ORP and sulfide profile after beginning micro-aeration at SOU at an air flow rate of 7 ml/min and an ORP set point of −10 mV in accordance with Example 1 (error bars indicate standard deviation of at least 5 consecutive data points).

FIG. 4 and Table 1 show the experimental results. During the experiment, HRTs of the bioreactor and SOU were controlled at 20 d and 2 hr, respectively. Biogas recirculation rate of 1.5 L/min was used for bioreactor mixing. The gas recirculation rate in SOU was 0.5 L/min. Air injection rate was controlled at 5 ml/min.

In general, biogas production rate increased, which in part was resulted from air injection. However, methane production after micro-aeration was comparable to that before micro-aeration. The percentage of methane slightly decreased. The percentage of nitrogen increased from approximately 1-2% to 10-12% while the percentage of carbon dioxide remained nearly constant.

After micro-aeration, ORPs in the bioreactor and SOU increased approximately 30 and 200 mV from approximately −270 and −440 mV, respectively (Table 1). Before micro-aeration, the average sulfide levels in bioreactor and SOU effluent was approximately 9.0 mg-S/L; however, after micro-aeration, the sulfide concentration decreased approximately by almost 70%. Before micro-aeration, hydrogen sulfide in bioreactor headspace and downstream from SOU was 3,100 $ppm_v$ on average. However, after micro-aeration, hydrogen sulfide decreased to approximately 11 $ppm_v$ in bioreactor headspace and less than 1 $ppm_v$ in downstream from SOU, which was more than 99.5% reduction. More importantly, percentage of oxygen in the bioreactor headspace and in the downstream from SOU was never above the detection limit (0.1%).

TABLE 1

ORP and sulfides (liquid and gas phase) at various points of the system.

| | Before micro-aeration | After micro-aeration |
|---|---|---|
| | ORP, mV | ORP, mV |
| Bioreactor | −472 ± 12[Ψ] | Bioreactor −440 ± 15 |
| SOU | −460 ± 15 | SOU −469 ± 17 |
| | Sulfide (liquid phase), mg/L as S | Sulfide (liquid phase), mg/L as S |
| Influent | 2.2 ± 1.5 | Influent 2.2 ± 1.5 |
| Bioreactor effluent | 8.8 ± 3.4 | Bioreactor effluent 3.2 ± 2 |
| SOU effluent | 9.4 ± 3.0 | SOU effluent 3.3 ± 2 |
| | Hydrogen sulfide (gas phase), $ppm_v$ | Hydrogen sulfide (gas phase), $ppm_v$ |
| Bioreactor headspace | 3,160 ± 280 | Bioreactor headspace 11 ± 4 |
| Upstream from SOU | 3,120 ± 250 | Upstream from SOU 6 ± 2 |
| Downstream from SOU | 3,050 ± 85 | Downstream from SOU <1 |

[Ψ]indicates standard deviation of at least 5 consecutive data points

EXAMPLE 2

A Pilot-Scale Study of Micro-Aeration for Sulfide Removal in Anaerobic Treatment of High-Solid Wastewater The pilot-scale facility consisted of a one-liter sulfide oxidizing unit (SOU) integrated with an anaerobic digester, a continuous stirred tank reactor (CSTR) with an internal settling zone with a working volume of 92 L. The effluent from the digester was pumped out of the system into the SOU to provide medium for sulfide removal.

Sulfide-laden biogas produced in the digester was mixed with small amount of air before being forced through a diffuser located at the bottom of the SOU. In the SOU, sulfide and oxygen flowed upward in a countercurrent direction against the digester effluent, where the formation of elemental sulfur took place. The elemental sulfur produced was collected in the bottom of the SOU and discharged periodically. Sulfide-free biogas was re-circulated back to the digester to scavenge the newly formed sulfide and brought back to SOU again. The cycle was repeated. Hydraulic retention times (HRTs) of the pilot scale digester and the SOU were controlled at 20 days and 4 hrs, respectively. the digester was continuously mixed by means of biogas recirculation at the rate of 1.5 L/min (0.016 $L/L_{digester}$-min) whereas the biogas recirculation rate of the SOU will be 0.5 $L/L_{sou}$-min). The integrated system will be operated at a room temperature of 25±2° C. the organic loading and COD rate to the digester were approximately 0.8 g-VS/L-day and 1.2 g-COD/L-day, respectively (Table 2).

TABLE 2

| Parameters | |
|---|---|
| TS, g/L | 21.1 ± 2.4 |
| VS, g/L | 15.5 ± 1.5 |
| Alkalinity, g/L as $CaCO_3$ | 1.3 ± 0.3 |
| pH | 6.5 ± 0.7 |
| TCOD, g/L | 24.2 ± 2.5 |
| SCOD, g/L | 3.4 ± 0.6 |
| $SO_4^{-2}$, mg/L | 122 ± 8 |
| Sulfides, mg/L | $ND^1$ |
| $S_2O_3^{2-}$, mg/L | ND |

[1]ND = Not detected

Aeration Control.

Two sets of pH and ORP probes were installed on top of the digester and SOU. Every minute, the ORP/pH controller will receive signal from the ORP and pH electrodes at SOU and respond to the change of the ORP. Depending on the ORP set point, the response will be either ON or OFF the solenoid valve that OPEN (injecting air) or CLOSE (stop injecting air), respectively. The actual air flow into the SOU will also be monitored with a flow meter. A computer is used as data acquisition system for better monitoring and recording necessary outputs. During the beginning of aeration, the aeration of controlled by ORP set points. However, later on, continuous aeration method (5 ml/min) was used and the ORP changes were monitored.

Startup.

The digester was inoculated with anaerobic digester sludge from a local wastewater treatment plant and fed with synthetic organic substrate. 15 liters of the synthetic organic substrate consist of 338.1 g of commercial dog food (with minimum 27% of crude protein, 50 g of $NaHCO_3$, and 15 ml of trace element solution (prepared by adding 10 g of $FeCl_2.4H_2O$, 2.0 g of $CoCl_2.6H_2O$, 1.0 g of EDTA, 500 mg of $MnCl_2.4H_2O$, 200 mg of Resazurin, 142 mg of $NiCl_2.6H_2O$, 123 mg of $Na_2SeO_3$, 90 mg of $AlCl_3.6H_2O$, 50 mg of $H_3BO_3$, 50 mg of $ZnCl_2$, 50 mg of $(NH_4)_6MoO_{24}.4H_2O$, 38 mg of $CuCl_2.2H_2O$, and 1.0 ml of HCl (37.7% solution) to distilled water to make 1 liter). Substrate preparation was conducted by soaking of dog food for 1 day, adding $NaHCO_3$ and trace element solution, and adjusting the volume to 15 L by tap water. The substrate was kept in a 4° C. refrigerator prior to feeding. Table 2 shows the chemical analysis of the substrate.

Steady State.

After more than six months after digester start-up, the SOU was connected to the digester as shown in FIG. 2. The testing of the integrated system was not conducted until the system was in steady state, which was approximately three months after. After all experiments under no aeration condition were completed, the system was subjected to aeration. The testing of the system under aeration condition was not conducted until another steady state was reached, which was approximately another three-month period.

Batch Experiments

Biomass Preparation.

Because of the long time required to collect biomass from the SOU, the biomass was obtained by using a tube attaching between the effluent port of the SOU and a bottle that had been flushed with 60:40% of $N_2/CO_2$ gas mixture to simulate the condition found in the integrated system. To minimize the exposure to oxygen in the air, biomass from the digester was taken just before the experiment. Regardless of where biomass came from, the biomass concentration in batch bottles was set to be 2 and 1 g-VS/L for methanogenic/sulfogenic activity and specific oxygen uptake rate tests, respectively. To achieve the biomass concentration in each bottle, appropriated volume of reactor content was centrifuged at 3600×g to obtain concentrated biomass. After discarding the supernatant, the biomass was then mixed with appropriate amount of nutrient solution (prepared by adding 7.95 g of $NaH_2PO_4.H_2O$, 6.0 g of $K_2HPO_4$, 2.8 g of $NH_4Cl$, 1.0 g of $MgSO_4.7H_2O$, 1.0 g of yeast extracts, 0.1 g of $CaCl_2$, and 10 ml of trace element solution (above) to deoxygenated distilled water to make 1 liter, resuspended using vortex mixer, and inoculated into each bottle.

Methanogenic Activities.

The methanogenic activity tests (SMA) were conducted by using either 250-ml or 500-ml total volume batch bottles with active volume of 150 ml (total volume of 280 and 610 ml, respectively). For methanogenic activity test using acetate and glucose as substrate, the 250-ml serum bottles were inoculated with concentrated biomass mixed with 15 ml of nutrient solution, acetate or glucose (2.0 g COD/L in the bottles), alkalinity (3.3 g/L as $CaCO_3$ in the bottles), and deoxygenated distilled water to make 150 ml. After adjusting pH to 7.0, the bottles were flushed with 80:20% of $N_2/CO_2$ gas mixture and capped with rubber septum. For methanogenic activity test using hydrogen as substrate, the 500-ml serum bottles were inoculated with the same amount of chemicals and biomass as in methanogenic activity test without adding glucose or sodium acetate. After adjusting pH to 7.0, the bottles were flushed with 80:20% of H2/CO2 gas mixture, capped with rubber septum, and injected with 128 ml of 80:20% of H2/CO2 gas mixture to result in 2 g COD/L in the bottles. All the bottles were incubated in room temperature (25±2° C.) on a shaker rotating at 180 rpm. All the experiments were duplicated.

Methane Production Estimation.

For bottles using acetate and glucose as substrate, biogas production and methane concentration were measured periodically using wetted syringe and gas chromatograph, respectively. To estimate the amount of methane production, the following equation was used:

$$\text{Methane production (ml)} = [(M_1V_1) + (M_1V_H) - (M_0V_H)]/100$$

where $M_1$ and $M_0$=methane concentration at the current time and at the previous time, respectively; $V_1$=volumetric biogas production; $V_H$=head space volume of the serum bottle, which is equal to 130 ml.

For bottles using hydrogen as substrate, after the pressure in bottles became negative, $N_2$ was injected into bottle until the pressure was equal to atmosphere. Then, methane concentration was measured, and the methane production was estimated using the following equation:

$$\text{Methane production (ml)} = [(M_1V_1) - (M_0V_H)]/100$$

where $V_H$=head space volume of the serum bottle, which is equal to 460 ml. When the bottles had positive pressure, the first equation to estimate methane production was used. The cumulative methane productions were plot against experimental time, and the methane production rate was estimated from the highest slope.

Sulfidogenic Activities.

The sulfidogenic activity tests (SA) were conducted the same was as methanogenic activity except $K_2SO_4$ (3.0 g/L in the bottles) and Bromoethane sulfonic acid (BES), 98% (50 mM in the bottles) were added into the bottles as a source of sulfate and methane inhibitor, respectively. Sodium acetate, glucose, or hydrogen was used as substrate (2 g COD/L in the bottles). The COD/$SO_4^{2-}$ ratio in each bottle was at 0.67 to minimize the methanogenic activity (Patidar, S. K. and Tare, V, 2004). Periodically, samples were taken from the bottles to measure sulfate concentration. The sulfate reduction rate was estimated from the highest slope. All the experiments were duplicated.

Specific Oxygen Uptake Rate.

The specific oxygen uptake rate (SOUR) was conducted using BOD bottles with active volume of 300 ml. The bottles were inoculated with concentrated biomass mixed with 30 ml of nutrient solution, glucose (1.0 g COD/L in the bottles), alkalinity (0.8 g/L as $CaCO_3$ in the bottles), and aerated distilled water to make 300 ml. After adjusting pH to 7.0, dissolve oxygen (DO) probe was mounted on each bottle. The depletion of DO concentration was measured every minute to estimate SOUR. All the experiments were duplicated.

Analytical Methods

Methane, carbon dioxide, and nitrogen in the biogas were analyzed with a Gow Mac series 350 GC-TCD fitted with a 84-mm (3.3-in.) stainless-steel column packed with Porapak T (60/80 mesh) (GOW-MAC Instrument Company). Helium was used as the carrier gas at a flow rate of 35 mL/min. The temperatures of the injection port, oven, and detector were at 150, 50, and 100° C., respectively. Oxygen and hydrogen sulfide in the biogas were analyzed with a Gow Mac series 400 GC-TCD fitted with Chromosil '310 and Molesieve 18 80/100 (8 ft) column. Helium was used as the carrier gas at flow rate of 30 ml/min. The temperatures of the injection port, measured by BW defender multi-gas detector (D4-2002) and Draeger tubes (RAE system). All gas production data reported were standardized to standard temperature (0° C.) and pressure (760 mm Hg). Sulfate and thiosulfate were analyzed by ion chromatograph (Dionex model DX 500) with AN1 anionic column and ASRS® ULTRA II, 4 mm, suppressor (Dionex P/N 061561) at 50 mA suppressor conductivity. Sodium carbonate/bicarbonate eluent was used as mobile phase at conductivity at a flow rate of 1 ml/min. Dissolved oxygen (DO) was measured by Accumet® Research AR40 Benchtop Dissolved Oxygen Meter Kit. Volatile fatty acids (VFAs), Total solids (TS), Volatile solids (VS), aqueous sulfide, alkalinity, and COD measurements were made in accordance with the procedures listed in Standard Methods (APHA et al., 1995). The soluble COD (SCOD) was defined as the COD component that passed through a 0.45-µm pore size filter.

RESULTS AND DISCUSSION

Continuous Experiments

Micro-Aeration Experiment.

Figure 5:
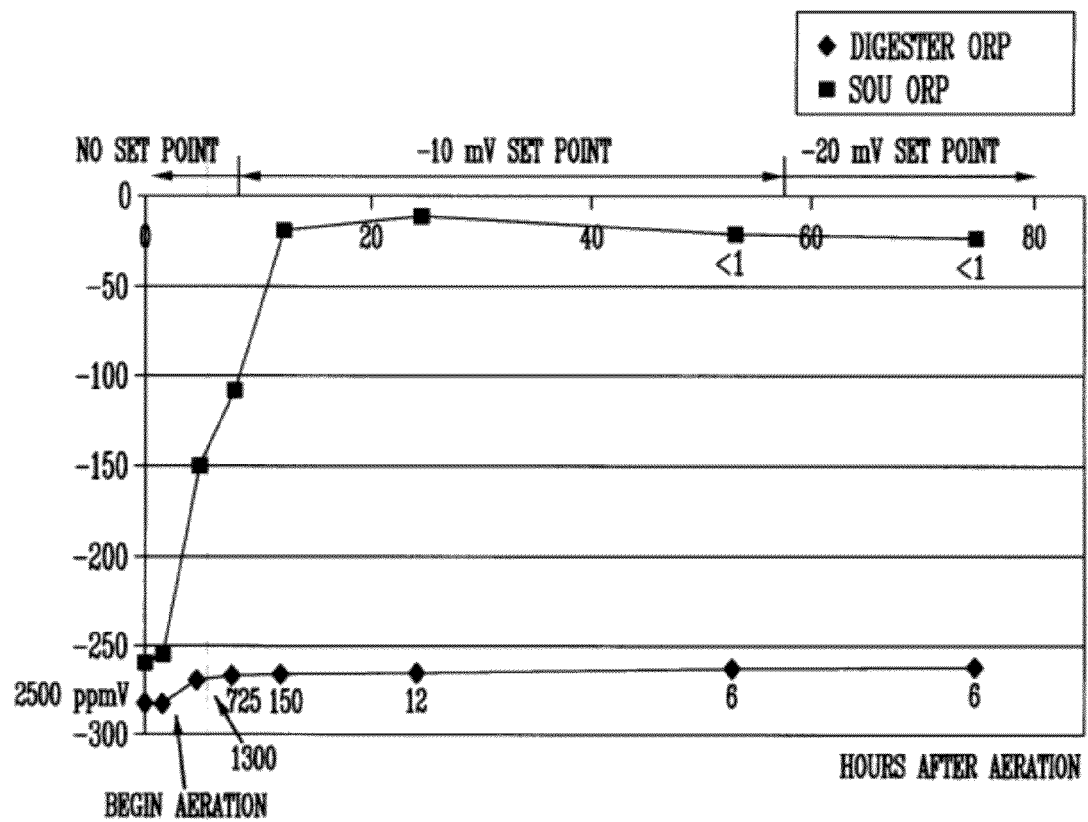
FIG. 5 illustrates the ORP and sulfide profile after beginning micro-aeration at SOU at an air flow rate of 7 ml/min with ORP at no set point, as described in Example 2.

In the beginning of the micro-aeration period of the continuous experiment, the aeration rate was arbitrarily set at 7 ml/min with ORP with no set point. Then, the set points were set at −10 and −20 mV. FIG. 5 shows ORP and $H_2S$ profiles of the SOU and digester during the beginning of the micro-aeration period. The numbers beside the data points represent hydrogen sulfide concentration at the time.

Figure 6:
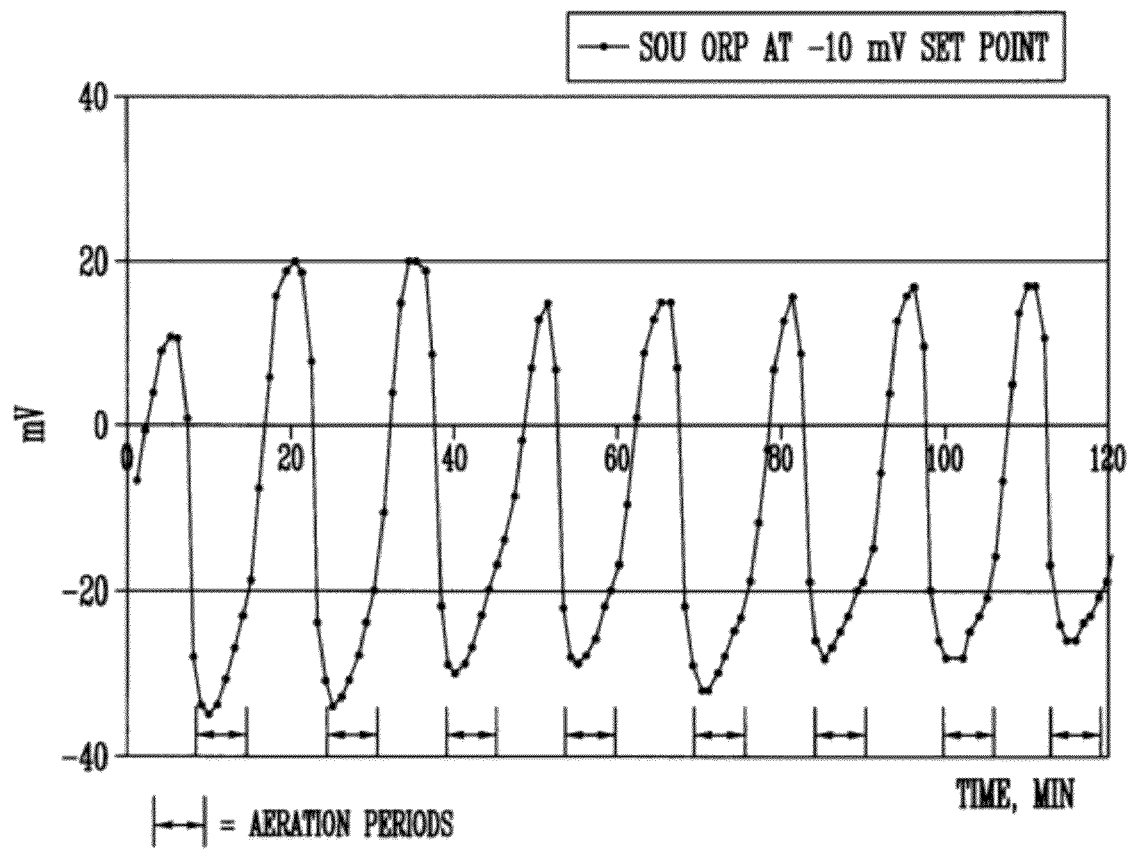
FIG. 6 illustrates the ORP profile of the SOU as set forth in Example 2.

It took merely 24 hours to reduce hydrogen sulfide in biogas at the SOU from 2500 to 3 ppmV and to less than 1 ppmV in the next day. The ORP of the SOU increased from −262 to the set points ORP of −10 and −20 mV. However, the ORP of the digester only went up 22 mV from −284 mV. FIG. 6 demonstrates 8 cycles of ORP profile of the SOU during a 2-hour period at −10 mV set point. Before the −10 mV set point was reached, aeration rate was at approximately at 7.0 ml/min (continuous aeration). During the −10 mV set point, aeration rate decreased to 3.1 ml/min and further decreased to 1.8 ml/min during the −20 mV set point (intermittent aeration). Because of less sulfide in the system, ORP did not decrease beyond the set point to trigger the solenoid valve to inject air into the SOU, resulting in less air requirement.

Optimizing Aeration Rate by ORP:

Optimization was conducted by varying the ORP set point to yield the minimum aeration required for hydrogen sulfide removal in biogas. The set points were set at −160 mV for 2 days, −210 mV for 1 day, −260 mV for 3 days, −270 mV for 2 days, −260 mV for 4 days, −210 mV for 1 day, −235 mV for 1 day, −220 mV for 1 day, −210 mV for 1 day, −190 mV for 1 day, and −170 mV for 1 day, respectively. Then, the ORP set points, the measured ORP, and hydrogen sulfide at SOU that corresponded to aeration rates are plotted from low to high (FIG. 7).

Figure 7:
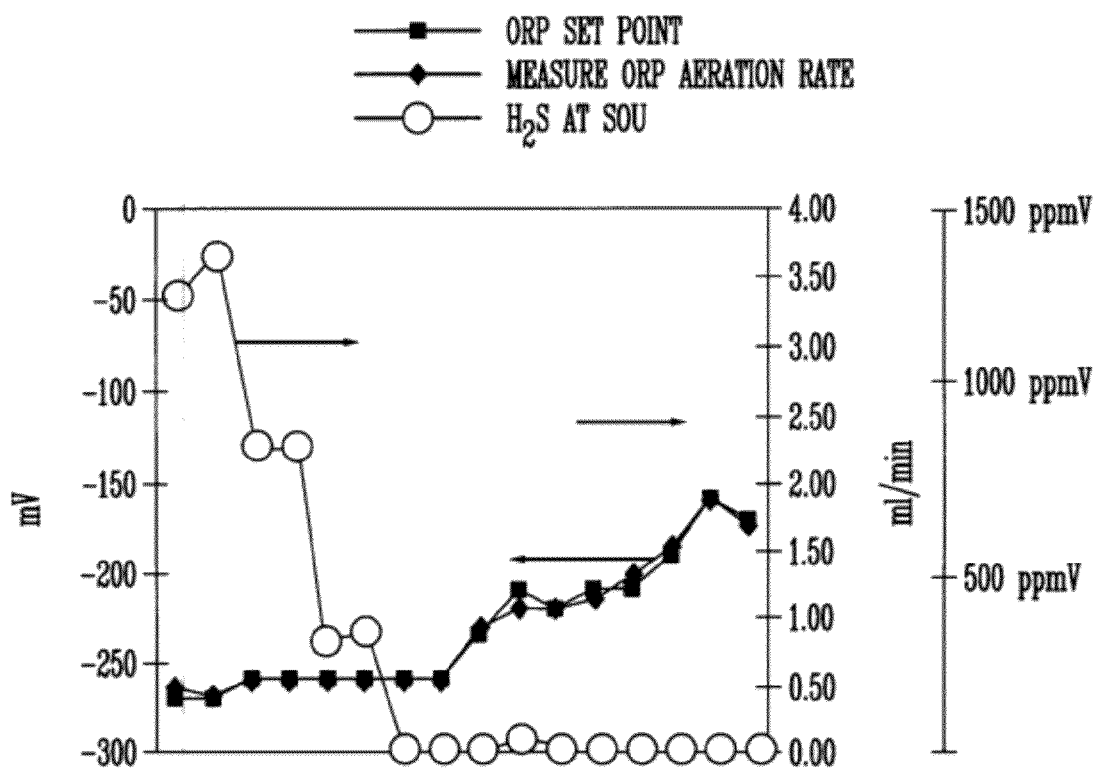
FIG. 7 illustrates the relationship of ORP, aeration rate, and hydrogen sulfide at the SOU, as set forth in Example 2.

From FIG. 7, the ORP of the SOU followed well with the ORP set point. Increase in aeration rates directly resulted in reduction in hydrogen sulfide at the SOU. For ORP set points higher than −260 mV, increased ORP set point resulted in increased aeration rate. However, at ORP set points of −260 mV or less, increase in aeration rate did not affect the ORP. It is suggested that the ORP set point and the aeration rate need to be more than −260 mV and 2.0 ml/min to successfully remove hydrogen sulfide from biogas by using the integrated system.

Long-Term Experiments:

During long-term operation, continuous aeration method was used to remove hydrogen sulfide from biogas. The goal was to find the minimum aeration rate that resulted in the lowest hydrogen sulfide in biogas at the SOU. ORP changes were monitored throughout the study. The resulting ORP can be used as a set point when needed. The aeration rates were varied between 2.0 to 6.0 ml/min during two months of experiment. It was found that aeration rate needs to be approximately 4.0-5.0 to ensure that the hydrogen sulfide in biogas at SOU was less than 5 ppmV. This aeration rate was more than 2.0 ml/min intermittent aeration. One of the reasons is that elemental sulfur formed in the SOU could possibly be reduced to hydrogen sulfide, adding extra load to the SOU. Therefore, the SOU required more air. Even at this high range of aeration rates, the ORP at the SOU was approximately −250 mV.

Comparison Experiments:

The comparison experiments between before and during micro-aeration were conducted at different periods of time, approximately six months apart. However, the system was operated in the same manner. the biogas production, percentage of methane, and the VFA in the reactor were approximately the same before the beginning of micro-aeration experiment. Air injection of 5 ml/min was chosen to be target continuous aeration rate. During the two experimental periods, all necessary tests were conducted for 7 days in a row. Table 3 shows the performance of the integrated system before and during micro-aeration from one experiment. From the results, while the biogas production rates of the two periods were different, the methane production rates were comparable. During micro-aeration, the hydrogen sulfide concentrations in the head space of SOU were never more than 4 ppmV and, most of the time, were less than a detection limit of 1 ppmV. The percentage of methane in biogas was slightly reduced as a result of nitrogen and oxygen addition during micro-aeration. The ORP levels of the digester and SOU increased from −277 and −261 mV to −265 and −246 mV, respectively. Dissolved sulfides in the effluents from both of the digester decreased by approximately 80%.

During micro-aeration, it was estimated that more than 98% of sulfide in gas and liquid phases was converted to elemental sulfur, which resulted in sulfide removal rate of 0.24 kg-S/$m^3$-sou/day. As mentioned before, in theory, the molar oxygen/sulfide consumption of the biological sulfide oxidation to elemental sulfur needs to be at 0.5. However, in this pilot-scale experiment, the oxygen consumption rate was 1.36 kg-$O_2$/$m^3$-sou/day, which resulted in the $O_2$/$S^{2-}$ of 5.6. In both conditions, COD and SCOD reductions were approximately 80 and 90%, respectively. VFA and alkalinity ratio were less than 0.03 in both cases.

TABLE 3

| | Before aeration | | After aeration | |
|---|---|---|---|---|
| | Reactor | SOU | Reactor | SOU |
| Biogas | | | | |
| $N_2$, % | 0.5 ± 0.1[1] | NT | 5.8 ± 0.8 | 6.8 ± 1.0 |
| $CH_4$, % | 65.6 ± 0.6 | NT | 63.3 ± 2.2 | 62.6 ± 2.4 |
| $CO_2$, % | 33.6 ± 1.1 | NT | 30.2 ± 1.3 | 29.8 ± 1.1 |
| $O_2$, % | $NT^2$ | NT | 0.4 ± 0.1 | 0.7 ± 0.1 |
| $H_2S$, ppmV | 2450 ± 150 | 2420 ± 170 | 29.0 ± 5.8 | 1.7 ± 1.7 |
| Biogas production, L/d | 54.2 ± 4.5 | | 59.8 ± 2.6 | |
| Methane production, L/d | 35.0 ± 0.6 | | 37.8 ± 0.1 | |
| Liquid | | | | |
| Sulfide, mg/L | 17.7 ± 1.7 | 17.4 ± 1.7 | 1.1 ± 1.1 | ND |
| Sulfate, mg/L | $ND^3$ | ND | 0.1 ± 0.2 | 12.5 ± 8.3 |
| Thiosulfate, mg/L | ND | ND | ND | ND |
| ORP, mV | −277 ± 8 | −261 ± 7 | −265 ± 12 | −246 ± 3 |
| pH | 7.17 ± 0.01 | 7.20 ± 0.01 | 7.24 ± 0.03 | 7.23 ± 0.01 |

[1] Standard deviation of seven data points
[2] NT = Not tested
[3] ND = Not detected Batch Experiment Methanogenic/sulfidogenic activities and specific oxygen uptake were studied using biomass from two different periods—with and without micro-aeration. The activity tests were to evaluate the performance of the different groups of biomass in both the digester and the SOU. Table 4 summarizes the results obtained from the batch experiments. The results showed no change in methanogenic activities utilizing different substrate. This confirms the results from continuous experiment that the methane production rates from the two conditions were similar. Even though, oxygen is considered toxic to methanogens, the amount of oxygen injected into the system was not high enough to cause toxicity. However, after air injection, the activities of sulfate reducing bacteria were increased, especially, the sulfate reducing bacteria using hydrogen as substrate—the activities were more than double. Specific oxygen uptake rates of the biomass in the digester at different conditions were similar; however, those of the biomass in the SOU were significantly different. The rate of the biomass in the SOU was almost triple, which indicated that aerobic or facultative bacteria were active.

TABLE 4

| | Before aeration | | After aeration | |
|---|---|---|---|---|
| | Reactor | SOU | Reactor | SOU |
| Methanogenic activities g-$CH_4$—COD/g-VS/day | | | | |
| Acetate | 0.21 ± 0.02 | 0.18 ± 0.01 | 0.25 ± 0.01 | 0.25 ± 0.01 |
| Glucose | 0.19 ± 0.02 | 0.16 ± 0.01 | 0.17 ± 0.01 | 0.15 ± 0.01 |
| Hydrogen | 0.49 ± 0.18 | 0.47 ± 0.01 | 0.48 ± 0.02 | 0.46 ± 0.10 |
| Sulfidogenic activities Mg—$SO_4$-red/g-VS/day | | | | |
| Acetate | 9.45 ± 0.81 | 8.98 ± 1.08 | 10.73 ± 0.61 | 10.14 ± 0.42 |
| Glucose | 45.08 ± 3.32 | 44.03 ± 3.24 | 47.39 ± 11.62 | 52.70 ± 1.70 |
| Hydrogen | 66.20 ± 13.39 | 66.41 ± 11.89 | 157.09 ± 18.04 | 192.39 ± 47.03 |

TABLE 4-continued

| | Before aeration | | After aeration | |
|---|---|---|---|---|
| | Reactor | SOU | Reactor | SOU |
| Specific oxygen uptake rates Mg—$O_2$/g-VS-hr glucose | 3.90 ± 0.07 | 2.67 ± 0.09 | 3.80 ± 0.15 | 7.52 ± 0.15 |

Conclusions

It was possible to use the integrated system to remove hydrogen sulfide from biogas (1-2 ppmV) with elemental recovery of more than 98% and minimal sulfate production. The activities of different groups of methanogens were not changed after micro-aeration, confirming the results that there was no deterioration of methane production rate in continuous experiment. The findings of this study are significant in providing preliminary design for integrated sulfide removal system that is efficient, robust, yet inexpensive.

For the above-stated reasons, it is submitted that the present invention accomplishes at least all of its stated objectives.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of treating wastewater and/or biogas to remove hydrogen sulfide by selective oxidation to elemental sulfur, comprising:
    digesting wastewater or biogas influent suspected of containing sulfide to produce substantially hydrogen sulfide-free effluent and/or biogas; and
    thereafter selectively oxidizing in a sulfide oxidizing unit diffuser at an oxygen/sulfide ratio of about 0.5 the biogas to elemental sulfur to minimize $So_4$=oxidation, and to reduce the hydrogen sulfide level in the wastewater or biogas to a level of <10 ppmV.

2. The method of claim 1 which includes the further step of separating the elemental sulfur from the hydrogen sulfide reduced level biogas.

3. The method of claim 1 whereby the SOU has a height of at least two (2) feet.

4. The method of claim 1 further including the step of bubbling the biogas into the SOU at a rate of about 0.05 to 5 L-biogas/$L_{sou}$-min.

5. The method of claim 1 whereby the SOU contains water.

6. The method of claim 1 hereby the biogas is oxidized by infusing air into the SOU.

7. The method of claim 1 whereby the SOU is monitored by an oxidation reduction potential (ORP) probe, said probe being connected to controllers that control the frequency and duration of air/oxygen injection into the SOU.

8. The method of claim 1 further including the step of removing the biogas that has been separated from the sulfur from the SOU and infusing said biogas back into the effluent.

9. The method of claim 8 whereby the biogas is infused into the digester at a rate of abut 0.0015 to 0.15 L-biogas/$L_{bioreactor}$-min.

10. The method of claim 1 whereby air or oxygen is injected into the SOU at a rate of 0.1 to 50% of the amount of biogas that is normally produced during the period with or without air/oxygen injection.

11. The method of claim 1 whereby the SOU does not include added media.

12. The method of claim 1 that is conducted without the use of added chemical oxidants or added microorganisms.

13. The method of claim 1 that removes hydrogen sulfide from the wastewater to a level of <1 ppmV.

14. The method of claim 1 that requires input of less than 2% oxygen to achieved wastewater hydrogen sulfide levels of <1 ppmV.

15. The method of claim 1 whereby the wastewater is high solids content of from about 2% to about 6% wastewater.

\* \* \* \* \*